United States Patent
Hidaka et al.

(10) Patent No.: US 8,114,008 B2
(45) Date of Patent: Feb. 14, 2012

(54) BLOOD PUMP AND PUMP UNIT

(75) Inventors: Tatsuya Hidaka, Hyogo-ken (JP);
Takeshi Okubo, Hyogo-ken (JP);
Yasuharu Yamamoto, Hyogo-ken (JP);
Toshiyuki Osada, Hyogo-ken (JP);
Masashi Tagawa, Hyogo-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 113 days.

(21) Appl. No.: 12/810,083

(22) PCT Filed: Jan. 22, 2009

(86) PCT No.: PCT/JP2009/050978
§ 371 (c)(1),
(2), (4) Date: Jun. 22, 2010

(87) PCT Pub. No.: WO2009/104451
PCT Pub. Date: Aug. 27, 2009

(65) Prior Publication Data
US 2010/0280305 A1 Nov. 4, 2010

(30) Foreign Application Priority Data

Feb. 22, 2008 (JP) ................................. 2008-042044

(51) Int. Cl.
*A61M 1/10* (2006.01)
(52) U.S. Cl. .......................... 600/16; 623/3.13; 623/3.14
(58) Field of Classification Search .......................... None
See application file for complete search history.

(56) References Cited

U.S. PATENT DOCUMENTS 3,647,314 A * 3/1972 Laessig ......................... 415/206
(Continued)

FOREIGN PATENT DOCUMENTS

DE 102006062170 A1 6/2007
(Continued)

OTHER PUBLICATIONS

German Office Action dated Aug. 8, 2011, issued in corresponding German Patent Application No. 112009001856.8.

(Continued)

*Primary Examiner* — Kennedy Schaetzle
(74) *Attorney, Agent, or Firm* — Westerman, Hattori, Daniels & Adrian, LLP; William F. Westerman

(57) ABSTRACT

Provided are a magnetic coupling as an axial bearing including a driven magnet (11B3) that is a permanent magnet provided to a rotating body (11) inside a casing (12) and a drive magnet (23A) that is a permanent magnet placed face to face with the driven magnet in a radial direction of the rotating body outside the casing to be magnetically coupled with the driven magnet, a driving motor (22) that rotatably drives the drive magnet about an axis (P) of the rotating body, a radial bearing that is a dynamic bearing having annular bearing surfaces (12B1, 11B1) centering on the axis on an inner wall of the casing and the rotating body, each of the annular bearing surfaces being arranged with a gap between the drive magnet and the driven magnet in the radial direction of the rotating body, and a closed impeller (11A) including a front shroud (11A1) arranged on a front side in the axis direction in the rotating body, a rear shroud (11A2) arranged on a rear side in the axis direction of the front shroud, and a vane (11A3) arranged between the front shroud and the rear shroud.

4 Claims, 4 Drawing Sheets

U.S. PATENT DOCUMENTS

| | | | | |
|---|---|---|---|---|
| 4,135,863 | A | * | 1/1979 | Davis et al. .................... 417/420 |
| 4,844,707 | A | * | 7/1989 | Kletschka ..................... 417/420 |
| 5,360,317 | A | * | 11/1994 | Clausen et al. ............... 415/206 |
| 5,575,630 | A | * | 11/1996 | Nakazawa et al. ............ 417/420 |
| 5,658,136 | A | * | 8/1997 | Mendler ....................... 417/420 |
| 6,100,618 | A | | 8/2000 | Schoeb et al. |
| 2006/0222533 | A1 | | 10/2006 | Reeves et al. |

FOREIGN PATENT DOCUMENTS

| | | |
|---|---|---|
| DE | 202006005189 U1 | 8/2007 |
| EP | 0184703 A1 | 6/1986 |
| JP | 7-136247 A | 5/1995 |
| JP | 8-71145 A | 3/1996 |
| JP | 11-503210 A | 3/1999 |
| JP | 2001-514532 A | 9/2001 |
| JP | 2002-315824 A | 10/2002 |
| JP | 2005-118237 A | 5/2005 |
| JP | 2006-226390 A | 8/2006 |
| WO | 97/49440 A3 | 12/1997 |

OTHER PUBLICATIONS

Japanese Office Action dated Nov. 9, 2010, issued in corresponding Japanese Patent Application No. 2008-042044.

International Search Report of PCT/JP2009/050978, mailing date of Apr. 28, 2009.

* cited by examiner

BLOOD PUMP AND PUMP UNIT

TECHNICAL FIELD

The present invention relates to a blood pump and a pump unit for pumping blood.

BACKGROUND ART

In open-heart surgery, a blood pump for pumping blood is used to maintain the blood circulation. A known blood pump includes a casing, an impeller rotatably arranged in the casing, and a driving mechanism causing the impeller to rotate, and causes the impeller to rotate by the driving mechanism to take blood into a channel inside the casing and pump the blood outside the casing.

In this type of blood pump, for example, a rotating shaft for the impeller penetrates the wall of the casing and projects from the casing, and a driving motor is connected to the rotating shaft. In an area where the rotating shaft penetrates the wall of the casing, an axial sealing structure is provided to prevent leakage of blood. However, because the axial sealing structure is in contact with the casing and the rotating shaft, red blood cells and other components in the blood may be damaged at these points of contact to cause hemolysis, and stagnant blood flow at the points of contact may cause a blood clot. In addition, an issue may arise with durability of the sealing.

To address the foregoing, a blood pump supporting an impeller in a casing in a noncontact manner has been known. Such a blood pump includes a driving mechanism that causes the impeller to rotate by interaction between a magnet provided to the impeller and another magnet arranged outside the casing and driven for rotation by a driving motor. In a narrow gap between the outer peripheral surface of the impeller and the inner peripheral surface of the casing, a dynamic bearing is provided that supports the impeller in the radial direction with the pressure of the blood pumped in through rotation of the impeller. Furthermore, a controllable magnetic bearing is provided that supports the impeller in the axis direction by placing a bearing magnet provided to the impeller and a magnet core provided to the casing face to face with each other in the radial direction and controlling the magnetic force of the magnet core depending on the position of the impeller (see Patent Document 1, for example).

[Patent Document 1] Japanese Patent Application Laid-open No. 2006-226390

DISCLOSURE OF INVENTION

Problem to be Solved by the Invention

In the blood pump disclosed in Patent Document 1, the impeller includes vanes radially arranged on one side surface in the axis direction of a base, and a channel for defining a dynamic bearing is formed on the other side of the base. The casing includes a suction tube toward the center on the one side of the base with the vanes, and an ejection tube on the outer peripheral surface. With this blood pump, the vanes produce outward pressure in the radial direction through rotation of the impeller, whereby blood is sucked through the suction tube and pumped out through the ejection tube.

In the blood pump thus configured, however, when blood is sucked on one side of the base with the vanes, the other side has higher pressure than the one side of the base, i.e., a pressure difference occurs therebetween, resulting in axial thrust load to push the impeller toward the one side. Consequently, the axial center gets misaligned to cause defective operation of the blood pump. While the controllable magnetic bearing supports the impeller in the axis direction in the blood pump disclosed in Patent Document 1, this involves high manufacturing cost for providing a control circuit and the magnetic core. In addition, malfunction of the control circuit leads to loss of the function of the bearing, which makes it difficult to ensure high reliability.

In view of the problems described above, the present invention has an object to provide a blood pump and a pump unit that are configured to rotatably supporting an impeller in a casing in the radial direction in a noncontact manner and to support axial thrust load at low manufacturing cost, thereby enabling rotation also in the axial direction in a noncontact manner.

Means for Solving Problem

According to an aspect of the present invention, a blood pump includes: a rotating body rotatably placed inside a casing a magnetic coupling functioning as an axial bearing including a driven magnet that is a permanent magnet provided to the rotating body and a drive magnet that is a permanent magnet placed face to face with the driven magnet in a radial direction of the rotating body outside the casing to be magnetically coupled with the driven magnet; a drive that rotatably drives the drive magnet about an axis of the rotating body; a radial bearing that is a dynamic bearing having annular bearing surfaces centering on the axis on an inner wall of the casing and the rotating body, each of the annular bearing surfaces being arranged with a gap between the drive magnet and the driven magnet in the radial direction of the rotating body; and a closed impeller including a front shroud arranged on a front side in the axis direction in the rotating body, a rear shroud arranged on a rear side in the axis direction of the front shroud, and a vane arranged between the front shroud and the rear shroud.

With this blood pump, because the radial bearing and the axial bearing cause the rotating body to rotate in a noncontact state with respect to the casing, states leading to hemolysis or a blood clot can be prevented without the need for any shaft penetrating the casing or any axial sealing structure to prevent leakage of blood along the shaft. Furthermore, the impeller of this blood pump includes the front shroud arranged on the front side in the axis direction through which blood is taken in, the rear shroud arranged on the rear side in the axis direction of the front shroud, and the vane arranged between the front shroud and the rear shroud. Therefore, the blood flowing toward the rear side of the rear shroud produces pressure acting on the front side in the axis direction, and the blood flowing toward the front side of the front shroud produces pressure acting on the rear side in the axis direction. Consequently, the balance of the axial thrust load pushing the impeller in the axis direction can be adjusted, whereby defective operation is prevented with a simple axial bearing having a driven magnet and a drive magnet alone. Manufacturing cost can be thus reduced because no control circuit for adjusting the magnetic force of a magnet core is required.

Advantageously, in the blood pump, the radial bearing is also arranged, besides between the rotating body and the inner wall of the casing on the rear side of the rear shroud that is between the drive magnet and the driven magnet, between the rotating body and the inner wall of the casing on the front side of the front shroud.

With this blood pump, the radial bearings support both ends of the rotating body. Therefore, the radial load of the rotating body can be held in a more stable manner.

Advantageously, in the blood pump, the blood pump is configured to have a pump unit in which the rotating body including the driven magnet is placed inside the casing, and the radial bearing is provided between the rotating body and the inner wall of the casing, and a driving unit that includes the drive magnet and the drive, and the pump unit is detachably provided to the driving unit.

With this blood pump, the pump unit is detachably provided to the driving unit. The pump unit, which comes in contact with blood, is thus disposable as a consumable supply. By providing the pump unit that is economical with this configuration, running cost to purchase consumable supplies can be reduced.

Advantageously, in the blood pump, the driven magnet is provided to a cylindrical shaft included in the rotating body, and the drive magnet is arranged outside in a radial direction of the shaft with respect to the driven magnet.

With this blood pump, the shaft can be made compact, and the pump unit can thus be made compact, which facilitates its handling.

According to another aspect of the present invention, a pump unit of a blood pump that includes a rotating body rotatably placed inside a casing and is detachably provided to a driving unit rotatably driving the rotating body, includes: a driven magnet that is a permanent magnet provided to the rotating body in a face-to-face manner in a radial direction of the rotating body with a drive magnet that is a permanent magnet of the driving unit provided outside the casing to be rotatably driven about an axis of the rotating body, the driven magnet being magnetically coupled with the drive magnet to be a magnetic coupling functioning as an axial bearing; a radial bearing that is a dynamic bearing having annular bearing surfaces centering on the axis on an inner wall of the casing and the rotating body, each of the annular bearing surfaces being arranged with a gap between the drive magnet and the driven magnet in the radial direction of the rotating body; and a closed impeller including a front shroud arranged on a front side in the axis direction in the rotating body, a rear shroud arranged on a rear side in the axis direction of the front shroud, and a vane arranged between the front shroud and the rear shroud.

With this pump unit, because the rotating body is caused to rotate in a noncontact state with respect to the casing by the radial bearing and the axial bearing, states leading to hemolysis or a blood clot can be prevented without the need for any shaft penetrating the casing or any axial sealing structure to prevent leakage of blood along the shaft. Furthermore, the impeller of this pump unit includes the front shroud arranged on the front side in the axis direction through which blood is taken in, the rear shroud arranged on the rear side in the axis direction of the front shroud, and the vane arranged between the front shroud and the rear shroud. Therefore, the blood flowing toward the rear side of the rear shroud produces pressure acting on the front side in the axis direction, and the blood flowing toward the front side of the front shroud produces pressure acting on the rear side in the axis direction. Consequently, the balance of the axial thrust load pushing the impeller in the axis direction can be adjusted, whereby defective operation is prevented with a simple axial bearing having a driven magnet and a drive magnet alone. Manufacturing cost can be thus reduced because no control circuit for adjusting the magnetic force of a magnet core is required.

Effect of the Invention

The present invention enables the impeller to be rotatably supported in the casing in a noncontact manner both in the axial direction and the radial direction with low manufacturing cost, and eliminates the need for controlling magnetic force, thereby ensuring high reliability.

EXPLANATIONS OF LETTERS OR NUMERALS 10 pump unit
11 rotating body
11A impeller
11A1 front shroud
11A1a suction port
11A1b cylindrical unit
11A1c bearing surface (radial bearing)
11A2 rear shroud
11A3 vane
11B shaft
11B1 bearing surface (radial bearing)
11B2 penetrating hole
11B3 driven magnet (axial bearing)
12 casing
12A pumping unit
12A1 suction inlet
12A2 ejection outlet
12A3 bearing surface (radial bearing)
12B bearing unit
12B1 bearing surface (radial bearing)
20 driving unit
21 container
22 driving motor (drive)
22A output shaft
23 rotating member
23A drive magnet (axial bearing)
24 lid member
24A recess
P axis

BEST MODE(S) FOR CARRYING OUT THE INVENTION

Embodiments of a blood pump and a pump unit according to the present invention will now be explained in detail with reference to the accompanying drawings. These embodiments are not intended to limit the present invention. Constituent elements in the embodiments below include elements readily substituted by those skilled in the art and substantially equivalent elements.

Figure 1:
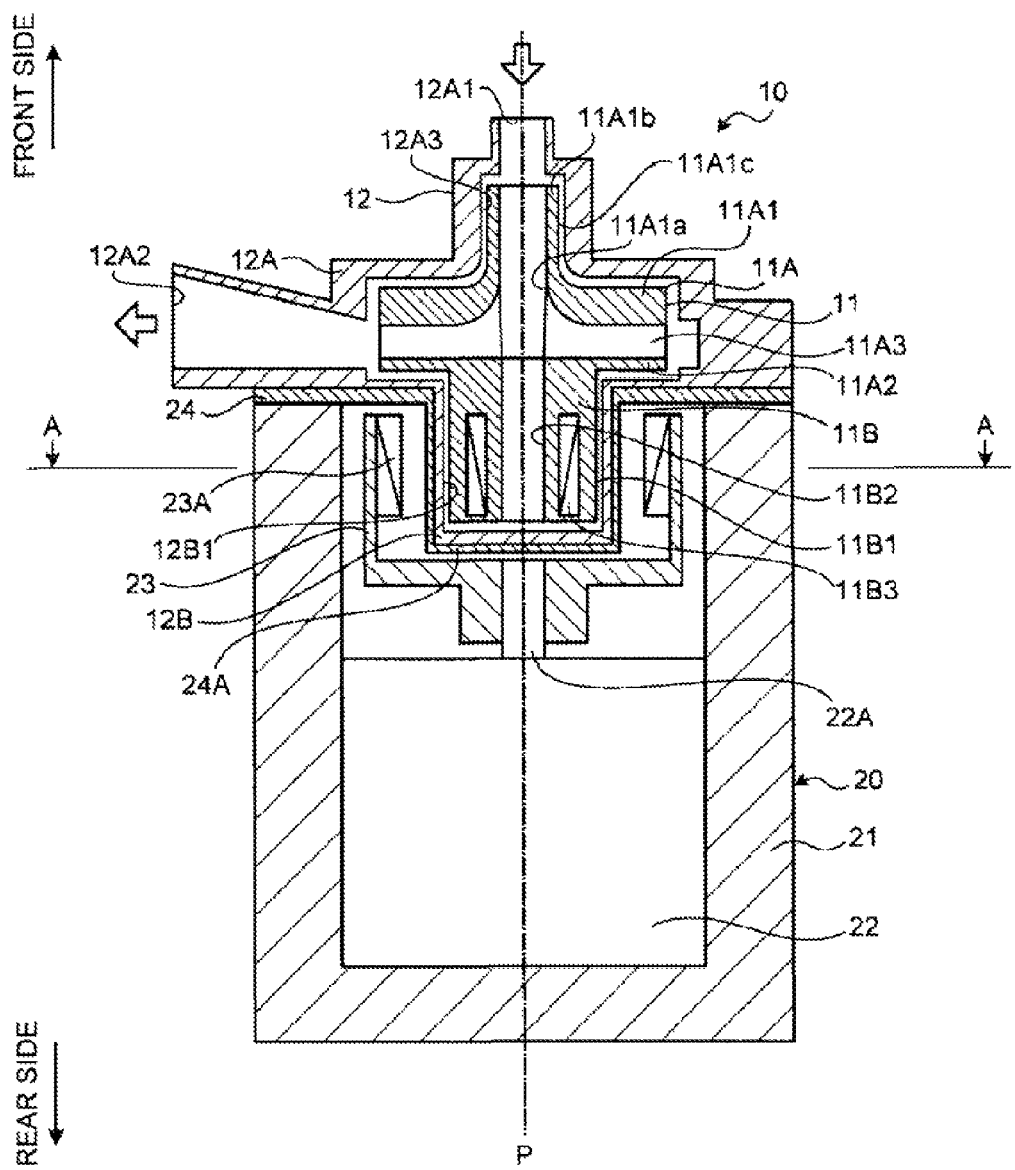
FIG. 1 is a schematic sectional view of a blood pump according to an embodiment of the present invention.
Figure 2:
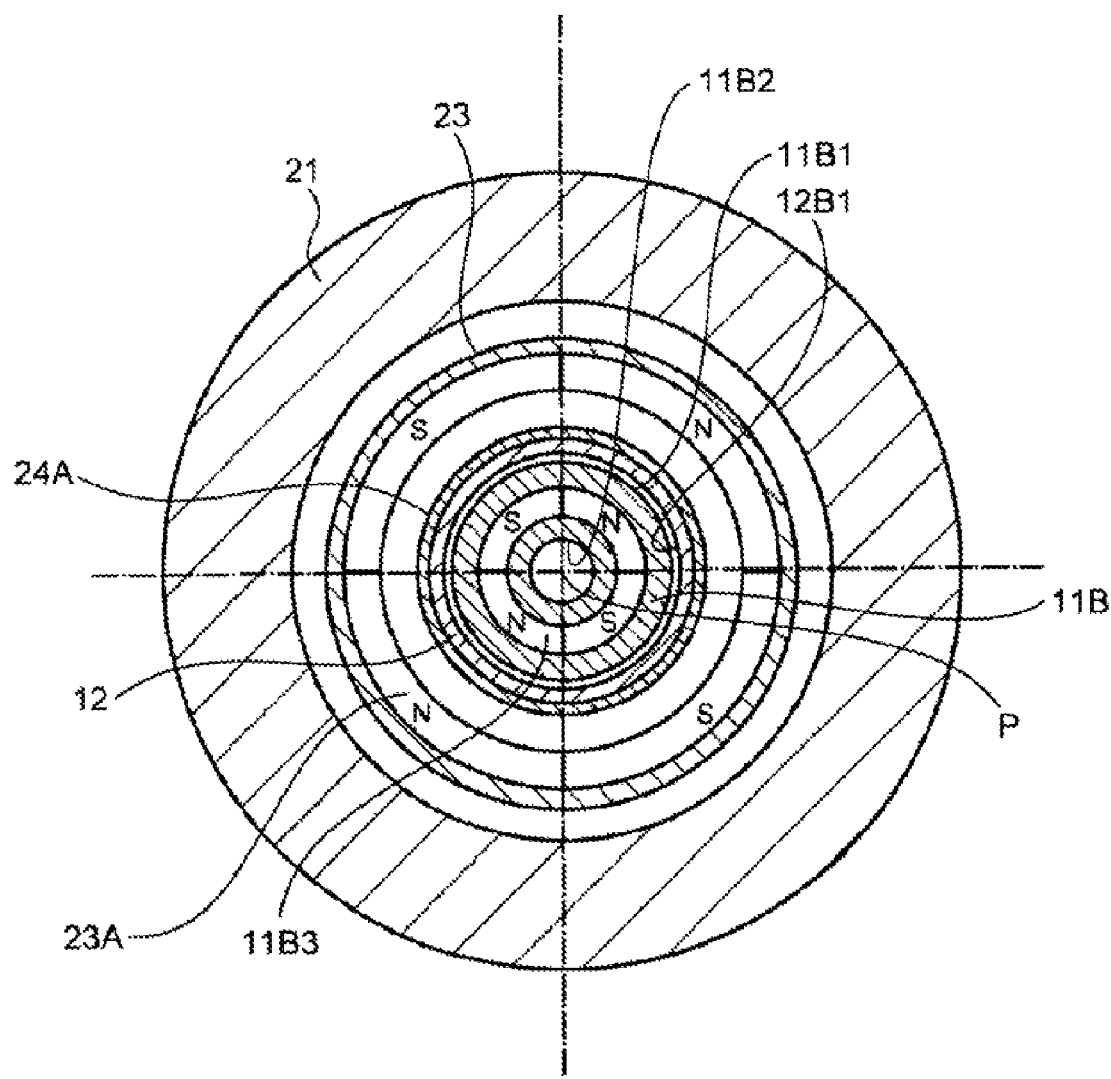
FIG. 2 is a sectional view along A-A in FIG. 1.
Figure 3:
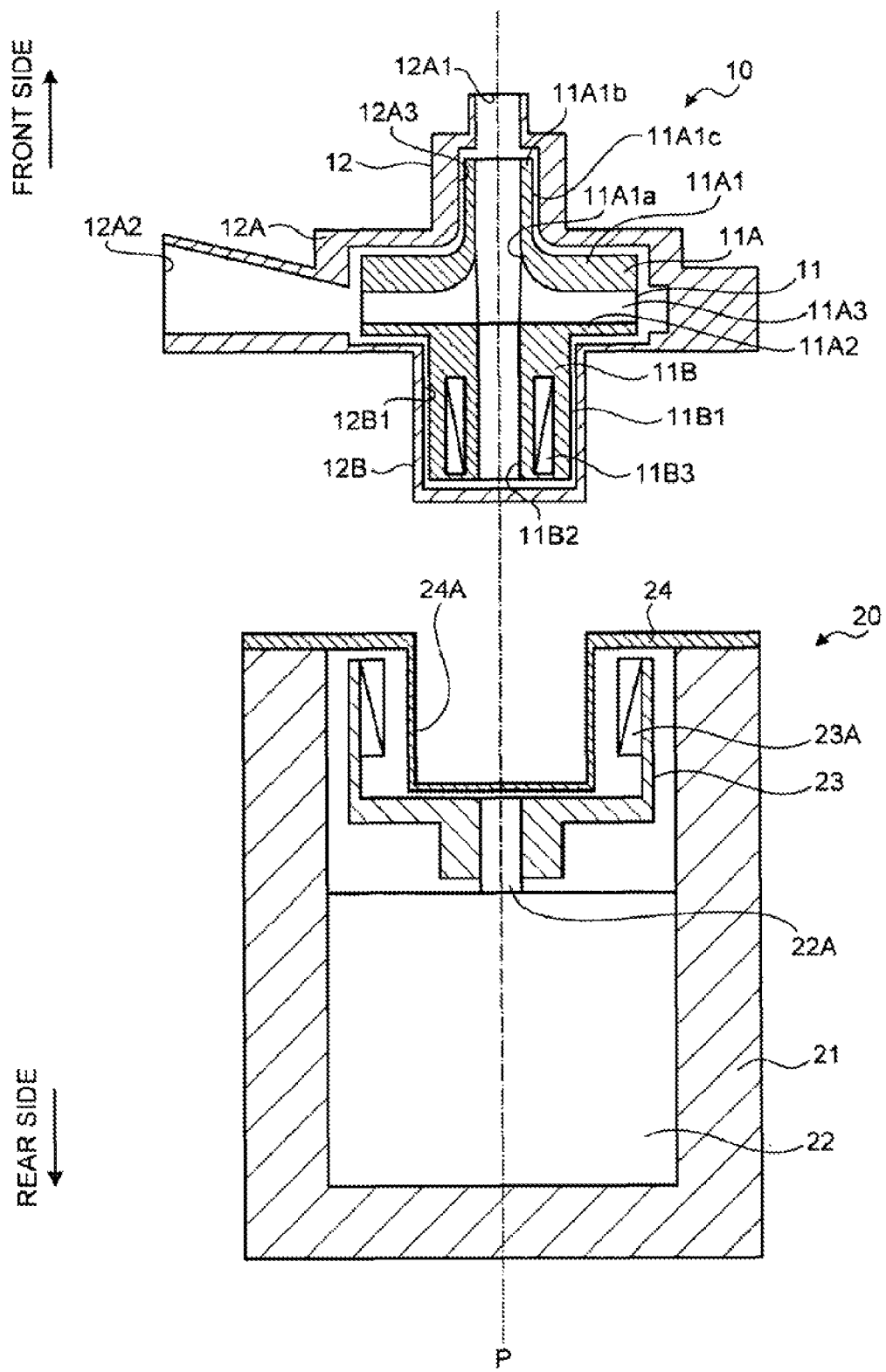
FIG. 3 is a schematic sectional view of the blood pump illustrated in FIG. 1 in a detached state.

FIG. 1 is a schematic sectional view of a blood pump according to an embodiment of the present invention. FIG. 2 is a sectional view along A-A in FIG. 1. FIG. 3 is a schematic sectional view of the blood pump illustrated in FIG. 1 in a detached state. As illustrated in FIG. 1, the blood pump according to the embodiment of the present invention includes a pump unit 10 and a driving unit 20.

The pump unit 10 includes a rotating body 11 and a casing 12.

The rotating body 11 has an impeller 11A and a shaft 11B. The impeller 11A is configured as a closed impeller having a front shroud 11A1, a rear shroud 11A2, and a vane 11A3. The front shroud 11A1 is formed in a substantially disk shape to define the outer diameter of a circle centering on an axis P about which the rotating body 11 rotates, and arranged on the front side in the axis P direction in the impeller 11A. The front shroud 11A1 has, along the axis P on which it centers, a suction port 11A1a penetrating therethrough for sucking blood. The rear shroud 11A2 is formed in a substantially disk shape to define the outer diameter of a circle centering on the axis P, and arranged on the rear side in the axis P direction (on the lower side of FIG. 1) in the impeller 11A. The vane 11A3 is placed in a gap between the front shroud 11A1 and the rear shroud 11A2. The vane 11A3 forms part of a spiral starting from the center and terminating at the outer peripheral end of the front shroud 11A1 to avoid the suction port 11A1a of the front shroud 11A1. A plurality of such vanes 11A3 is provided at regular intervals in the circumferential directions of the front shroud 11A1 and the rear shroud 11A2. The outer peripheral rims of the front shroud 11A1 and the rear shroud 11A2 that have high pressure during pumping of blood are arranged on the outermost periphery of the rotating body 11.

The shaft 11B is formed in a cylindrical shape having a smaller diameter than that of each shroud 11A1, 11A2 and centering on the axis P, and projects further toward the rear side in the axis P direction of the rear shroud 11A2. On the outer periphery of the shaft 11B, an annular bearing surface 11B1 centering on the axis P is formed. The shaft 11B also has, along the axis P on which it centers, a penetrating hole 11B2. The penetrating hole 11B2 is formed to penetrate the rear shroud 11A2 and to communicate with the suction port 11A1a of the front shroud 11A1 through the gap between the front shroud 11A1 and the rear shroud 11A2. A driven magnet 11B3 is also provided to the shaft 11B. The driven magnet 11B3 is a permanent magnet and is embedded in the shaft 11B along the bearing surface 11B1. A plurality of (e.g., four) such driven magnets 11B3 is formed in an annular shape centering on the axis P and is so arranged that S and N poles are alternately placed next to each other along the annular shape as illustrated in FIG. 2.

The casing 12 forms an outer casing of the pump unit 10 and contains therein the rotating body 11. The casing 12 has, on the front side in the axis P direction about which the rotating body 11 rotates, a suction inlet 12A1 for taking in blood. The casing 12 also has an ejection outlet 12A2 for pumping out blood to areas on the outer side in the radial direction of the impeller 11A perpendicular to the axis P.

The casing 12 includes a pumping unit 12A having an inner wall formed along the contour of the rotating body 11, enclosing the impeller 11A, and having the suction inlet 12A1 and the ejection outlet 12A2; and a bearing unit 12B enclosing the shaft 11B and projecting toward the rear side in the axis P direction of the pumping unit 12A. The casing 12 is formed to have a certain gap between its inner wall and the contour of the rotating body 11. In other words, the casing 12 is configured to have a noncontact operation state with respect to the rotating body 11 while containing therein the rotating body 11. On the inner wall of the bearing unit 12B of the casing 12, an annular bearing surface 12B1 centering on the axis P is placed face to face with the bearing surface 11B1 formed on the shaft 11B of the rotating body 11 with a certain gap in the radial direction of the rotating body 11 interposed therebetween.

The driving unit 20 is prepared by placing a driving motor (drive) 22 and a rotating member 23 in a bottomed cylindrical container 21. The driving motor 22 is fixed inside the container 21, and has an output shaft 22A extending toward the front side along the axis P of the rotating body 11. The rotating member 23 is fixed to the output shaft 22A of the driving motor 22 and provided rotatably about the axis P through driving of the driving motor 22. The rotating member 23 is formed in an annular shape centering on the axis P to enclose the bearing unit 12B of the casing 12 of the pump unit 10. In other words, the rotating member 23 encloses the shaft 11B of the rotating body 11 in the casing 12.

To the annular inner wall of the rotating member 23, a drive magnet 23A is provided. The drive magnet 23A is a permanent magnet. A plurality of (e.g., four) such drive magnets 23A is provided in an annular shape centering on the axis P and is so arranged that S and N poles are alternately placed next to each other along the annular shape as illustrated in FIG. 2. The drive magnet 23A is placed face to face with the driven magnet 11B3 in the radial direction of the rotating body 11, thereby being magnetically coupled with the driven magnet 11B3 provided to the shaft 11B of the rotating body 11 from outside of the casing 12.

On the front side in the axis P direction of the container 21, a lid member 24 is provided for hermetically closing the opening of the container 21 and covering the driving motor 22 and the rotating member 23. The lid member 24 has a recess 24A that is retracted in the annular shape of the rotating member 23. Into the recess 24A, the bearing unit 12B of the casing 12 is inserted to place the shaft 11B of the pump unit 10 in the annular shape of the rotating member 23. As illustrated in FIG. 3, the bearing unit 12B of the casing 12 is detachably provided to the recess 24A.

The blood pump thus configured drives, in a state where the bearing unit 12B of the casing 12 is inserted into the recess 24A of the lid member 24, the driving motor 22 to cause the rotating member 23 to rotate about the axis P. When the rotating member 23 rotates, the drive magnet 23A provided to the rotating member 23 rotates about the axis P. Along with this rotation, the driven magnet 11B3 magnetically coupled with the drive magnet 23A also rotates. When the driven magnet 11B3 rotates, the rotating body 11 provided with the driven magnet 11B3 rotates substantially about the axis P. In this operation, because the driven magnet 11B3 is magnetically coupled with the drive magnet 23A, suction force in the opposite direction to the movement in the axis P direction acts on the rotating body 11 provided with the driven magnet 11B3. In other words, the driven magnet 11B3 and the drive magnet 23A serve as a magnetic coupling functioning as an axial bearing that holds rotation of the rotating body 11 in the axis P direction.

When the rotating body 11 rotates, by the action of the vanes 11A3, blood is taken inside the casing 12 through the suction inlet 12A1. The blood is pumped through the suction port 11A1a of the impeller 11A into the gap between the front shroud 11A1 and the rear shroud 11A2, further pumped through this gap outward in the radial direction, and pumped outside the casing 12 through the ejection outlet 12A2.

Part of the high-pressure blood pumped outward in the radial direction through the gap between the front shroud 11A1 and the rear shroud 11A2 is not pumped outside the casing 12 through the ejection outlet 12A2, and circulates in a comparatively low pressure area near the axis P inside the casing 12. More specifically, on the outer periphery of the impeller 11A, the high-pressure blood flows through the gap between the front shroud 11A1 and the rear shroud 11A2 toward the front side of the front shroud 11A1 and the rear side of the rear shroud 11A2. The blood flowing toward the front side of the front shroud 11A1 passes between the front surface of the front shroud 11A1 and the inner wall of the casing 12 toward the axis P, and returns to the gap between the front shroud 11A1 and the rear shroud 11A2 through the suction port 11A1a. On the other hand, the blood flowing toward the rear side of the rear shroud 11A2 passes between the rear surface of the rear shroud 11A2 and the inner wall of the casing 12 toward the axis P, further passes through the gap between the bearing surface 11B1 of the shaft 11B and the bearing surface 12B1 of the casing 12, and returns to the gap between the front shroud 11A1 and the rear shroud 11A2 through the penetrating hole 11B2.

Because the gap between the bearing surface 11B1 and the bearing surface 12B1 is formed in an annular shape centering on the axis P, the blood passes through this gap, and the bearing surface 11B1 and the bearing surface 12B1 serve as a radial bearing as a dynamic bearing that holds rotation of the rotating body 11 about the axis P in the radial direction with the blood working as a lubricating fluid. In this manner, the shaft 11B is held in a position centering on the axis P. In other words, the radial position of the rotating body 11 is held in a noncontact state with respect to the casing 12.

Accordingly, with this blood pump, because the radial bearing and the axial bearing cause the rotating body 11 to rotate in a noncontact state with respect to the casing 12, states leading to hemolysis or a blood clot can be prevented without the need for any shaft penetrating the casing 12 or any axial sealing structure to prevent leakage of blood along the shaft.

In particular, the impeller 11A of the pump unit 10 in this blood pump includes the front shroud 11A1 arranged on the front side in the axis P direction through which blood is taken in, the rear shroud 11A2 arranged on the rear side in the axis P direction of the front shroud 11A1, and the vanes 11A3 arranged between the front shroud 11A1 and the rear shroud 11A2. Therefore, the blood flowing toward the rear side of the rear shroud 11A2 produces pressure acting on the front side in the axis P direction, and the blood flowing toward the front side of the front shroud 11A1 produces pressure acting on the rear side in the axis P direction. Consequently, the axial thrust load pushing the impeller 11A in the axis P direction can be adjusted, whereby defective operation is prevented with a simple axial bearing having the driven magnet 11B3 and the drive magnet 23A alone. Manufacturing cost can be thus reduced because no control circuit for adjusting the magnetic force of a magnet core is required.

With this blood pump, the pump unit 10 is detachably provided to the driving unit 20. The pump unit 10, which comes in contact with blood, is thus disposable as a consumable supply. By providing the pump unit 10 that is economical with this configuration, running cost to purchase consumable supplies can be reduced.

In the blood pump, the driven magnet 11B3 is provided to the shaft 11B formed in a cylindrical shape centering on the axis P, and the drive magnet 23A is placed on the outer side in the radial direction of the shaft 11B with respect to the driven magnet 11B3. Therefore, as illustrated by the blood pump in FIG. 4, the driven magnet 11B3 is provided to the shaft 11B formed in an annular shape centering on the axis P, and the shaft 11B and the bearing unit 12B can be made compact compared with a configuration in which the drive magnet 23A is placed on the inner side in the radial direction of the shaft 11B with respect to the driven magnet 11B3. Therefore, the pump unit 10 to be disposed as a consumable supply can be made compact, which facilitates its handling.

The blood pump according to the present embodiment includes a radial bearing each on the front side in the axis P direction and the rear side in the axis P direction of the rotating body 11. The radial bearing on the rear side in the axis P direction of the rotating body 11 is, as described above, the gap between the bearing surface 11B1 and the bearing surface 12B1 that is placed between the driven magnet 11B3 and the drive magnet 23A. The radial bearing on the front side in the axis P direction of the rotating body 11 is arranged on the front side of the front shroud 11A1, except for between the driven magnet 11B3 and the drive magnet 23A. More specifically, on the front side of the front shroud 11A1, a cylindrical unit 11A1b is formed to extend further toward the front side of the suction port 11A1a. On the outer periphery of the cylindrical unit 11A1b, an annular bearing surface 11A1c centering on the axis P is provided. On the other hand, on the inner wall of the pumping unit 12A of the casing 12, an annular bearing surface 12A3 centering on the axis P is placed face to face with the bearing surface 11A1c with a certain gap in the radial direction of the rotating body 11 interposed therebetween. The blood passes through the gap between the bearing surface 11A1c and the bearing surface 12A3, and the bearing surface 11A1c and the bearing surface 12A3 serve as a radial bearing as a dynamic bearing that holds rotation of the rotating body 11 about the axis P in the radial direction with the blood working as a lubricating fluid. In this manner, the impeller 11A is held in a position centering on the axis P. By thus providing the radial bearings on the front side in the axis P direction and the rear side in the axis P direction of the rotating body 11, the radial bearings support both ends of the rotating body 11. Therefore, the radial load of the rotating body 11 can be held in a more stable manner.

Figure 4:
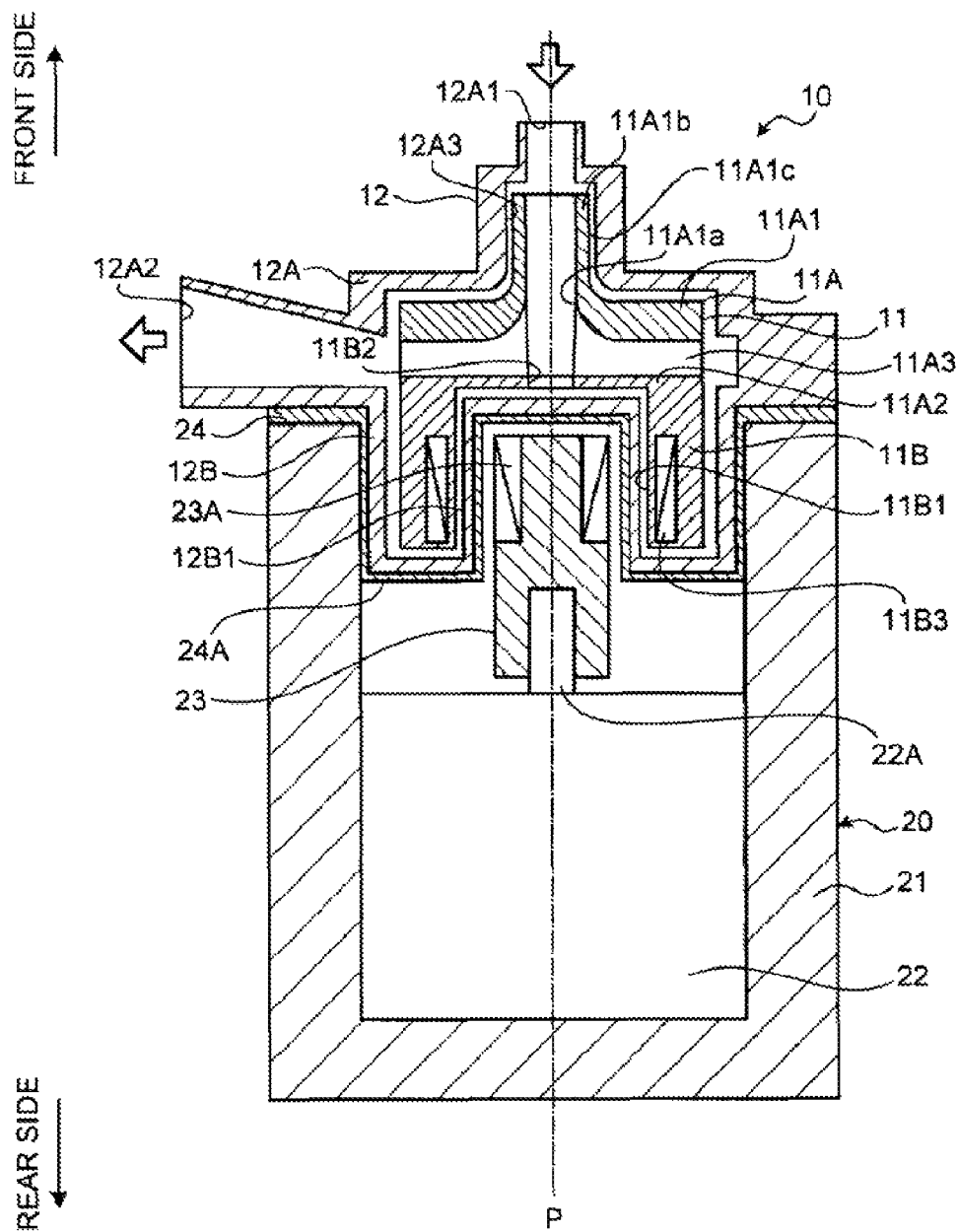
FIG. 4 is a schematic sectional view of a blood pump having an alternative structure according to the present embodiment.

A blood pump having an alternative structure will be described below. FIG. 4 is a schematic sectional view of a blood pump having an alternative structure according to the present embodiment. Regarding the blood pump having an alternative structure described below, elements that are equivalent to those included in the blood pump described above have the same reference numerals, and description will be made for differences therebetween.

This blood pump with an alternative structure differs from the blood pump described above in: the configuration of the shaft 11B of the rotating body 11 in the pump unit 10, the configuration of the bearing unit 12B of the casing 12 that the shaft 11B involves, the configuration of the rotating member 23 in the driving unit 20, and the configuration of the lid member 24 that the rotating member 23 involves.

In the rotating body 11 of the pump unit 10, the shaft 11B is formed in an annular shape centering on the axis P, and projects further toward the rear side in the axis P direction of the rear shroud 11A2. On the inner periphery of the shaft 11B, the annular bearing surface 11B1 centering on the axis P is formed. The driven magnet 11B3 is also provided to the shaft 11B. The driven magnet 11B3 is a permanent magnet and is embedded in the shaft 11B along the bearing surface 11B1. A plurality of such driven magnets 11B3 is formed in an annular shape centering on the axis P and is so arranged that S and N poles are alternately placed next to each other along the annular shape. On the center of the rear shroud 11A2 to which the shaft 11B is provided protrudingly, the penetrating hole 11B2 is formed along the axis P. The penetrating hole 11B2 is provided to penetrate the rear shroud 11A2 and to communicate with the suction port 11A1a of the front shroud 11A1 through the gap between the front shroud 11A1 and the rear shroud 11A2.

The casing 12 is formed to have a certain gap between its inner wall and the contour of the rotating body 11. In other words, the casing 12 is configured to have a noncontact operation state with respect to the rotating body 11 while containing therein the rotating body 11. On the inner wall of the bearing unit 12B of the casing 12, the annular bearing surface 12B1 centering on the axis P is placed face to face with the bearing surface 11B1 formed on the shaft 11B of the rotating body 11 with a certain gap in the radial direction of the rotating body 11 interposed therebetween.

The rotating member 23 in the driving unit 20 is fixed to the output shaft 22A of the driving motor 22 and provided rotatably about the axis P through driving of the driving motor 22. The rotating member 23 is formed in a cylindrical shape centering on the axis P to come inside the annular shape of the bearing unit 12B of the casing 12. In other words, the rotating member 23 comes inside the annular shape of the shaft 11B of the rotating body 11.

To the cylindrical outer wall of the rotating member 23, the drive magnet 23A is provided. The drive magnet 23A is a permanent magnet. A plurality of such drive magnets 23A is formed in an annular shape centering on the axis P and is so arranged that S and N poles are alternately placed next to each other along the annular shape. The drive magnet 23A is placed face to face with the driven magnet 11B3 in the radial direction of the rotating body 11, thereby being magnetically coupled with the driven magnet 11B3 provided to the shaft 11B of the rotating body 11 from outside of the casing 12.

On the front side in the axis P direction of the container 21, the lid member 24 is provided for hermetically closing the opening of the container 21 and covering the driving motor 22 and the rotating member 23.

The lid member 24 has the recess 24A in an annular shape surrounding the cylindrical shape of the rotating member 23. Into the recess 24A, the bearing unit 12B of the casing 12 is inserted to place the shaft 11B of the pump unit 10 outside the cylindrical shape of the rotating member 23. The bearing unit 12B of the casing 12 is detachably provided to the recess 24A.

The blood pump thus configured drives, in a state where the bearing unit 12B of the casing 12 is inserted into the recess 24A of the lid member 24, the driving motor 22 to cause the rotating member 23 to rotate about the axis P. When the rotating member 23 rotates, the drive magnet 23A provided to the rotating member 23 rotates about the axis P. Along with this rotation, the driven magnet 11B3 magnetically coupled with the drive magnet 23A also rotates. When the driven magnet 11B3 rotates, the rotating body 11 provided with the driven magnet 11B3 rotates substantially about the axis P. In this operation, because the driven magnet 11B3 is magnetically coupled with the drive magnet 23A, suction force in the opposite direction to the movement in the axis P direction acts on the rotating body 11 provided with the driven magnet 11B3. In other words, the driven magnet 11B3 and the drive magnet 23A serve as a magnetic coupling functioning as an axial bearing that holds rotation of the rotating body 11 in the axis P direction.

When the rotating body 11 rotates, by the action of the vanes 11A3, blood is taken inside the casing 12 through the suction inlet 12A1. The blood is pumped through the suction port 11A1a of the impeller 11A into the gap between the front shroud 11A1 and the rear shroud 11A2, further pumped through this gap outward in the radial direction, and pumped outside the casing 12 through the ejection outlet 12A2.

Part of the high-pressure blood pumped outward in the radial direction through the gap between the front shroud 11A1 and the rear shroud 11A2 is not pumped outside the casing 12 through the ejection outlet 12A2, and circulates in a comparatively low pressure area near the axis P inside the casing 12. More specifically, on the outer periphery of the impeller 11A, the high-pressure blood flows through the gap between the front shroud 11A1 and the rear shroud 11A2 toward the front side of the front shroud 11A1 and the rear side of the rear shroud 11A2. The blood flowing toward the front side of the front shroud 11A1 passes between the front surface of the front shroud 11A1 and the inner wall of the casing 12 toward the axis P, and returns to the gap between the front shroud 11A1 and the rear shroud 11A2 through the suction port 11A1a. On the other hand, the blood flowing toward the rear side of the rear shroud 11A2 passes between the rear surface of the rear shroud 11A2 and the inner wall of the casing 12 toward the axis P, further passes through the gap between the bearing surface 11B1 of the shaft 11B and the bearing surface 12B1 of the casing 12, and returns to the gap between the front shroud 11A1 and the rear shroud 11A2 through the penetrating hole 11B2.

Because the gap between the bearing surface 11B1 and the bearing surface 12B1 is formed in an annular shape centering on the axis P, the blood passes through this gap, and the bearing surface 11B1 and the bearing surface 12B1 serve as a radial bearing as a dynamic bearing that holds rotation of the rotating body 11 about the axis P in the radial direction with the blood working as a lubricating fluid. In this manner, the shaft 11B is held in a position centering on the axis P. In other words, the radial position of the rotating body 11 is held in a noncontact state with respect to the casing 12.

Accordingly, with this blood pump, because the radial bearing and the axial bearing cause the rotating body 11 to rotate in a noncontact state with respect to the casing 12, states leading to hemolysis or a blood clot can be prevented without the need for any shaft penetrating the casing 12 or any axial sealing structure to prevent leakage of blood along the shaft.

In particular, the impeller 11A of the pump unit 10 in this blood pump includes the front shroud 11A1 arranged on the front side in the axis P direction through which blood is taken in, the rear shroud 11A2 arranged on the rear side in the axis P direction of the front shroud 11A1, and the vanes 11A3 arranged between the front shroud 11A1 and the rear shroud 11A2. Therefore, the blood flowing toward the rear side of the rear shroud 11A2 produces pressure acting on the front side in the axis P direction, and the blood flowing toward the front side of the front shroud 11A1 produces pressure acting on the rear side in the axis P direction. Consequently, the axial thrust load pushing the impeller 11A in the axis P direction can be adjusted, whereby defective operation is prevented with a simple axial bearing having the driven magnet 11B3 and the drive magnet 23A alone. Manufacturing cost can be thus reduced because no control circuit for adjusting the magnetic force of a magnet core is required.

With this blood pump, the pump unit 10 is detachably provided to the driving unit 20. The pump unit 10, which comes in contact with blood, is thus disposable as a consumable supply. By providing the pump unit 10 that is economical with this configuration, running cost to purchase consumable supplies can be reduced.

The blood pump according to the present embodiment includes a radial bearing each on the front side in the axis P direction and the rear side in the axis P direction of the rotating body 11. The radial bearing on the rear side in the axis P direction of the rotating body 11 is, as described above, the gap between the bearing surface 11B1 and the bearing surface 12B1 that is placed between the driven magnet 11B3 and the drive magnet 23A. The radial bearing on the front side in the axis P direction of the rotating body 11 is arranged on the front side of the front shroud 11A1, except for between the driven magnet 11B3 and the drive magnet 23A. More specifically, on the front side of the front shroud 11A1, a cylindrical unit 11A1b is formed to extend further toward the front side of the suction port 11A1a. On the outer periphery of the cylindrical unit 11A1b, an annular bearing surface 11A1c centering on the axis P is provided. On the other hand, on the inner wall of the pumping unit 12A of the casing 12, an annular bearing surface 12A3 centering on the axis P is placed face to face with the bearing surface 11A1c with a certain gap in the radial direction of the rotating body 11 interposed therebetween. The blood passes through the gap between the bearing surface 11A1c and the bearing surface 12A3, and the bearing surface 11A1c and the bearing surface 12A3 serve as a radial bearing as a dynamic bearing that holds rotation of the rotating body 11 about the axis P in the radial direction with the blood working as a lubricating fluid. In this manner, the impeller 11A is held in a position centering on the axis P. By thus providing the radial bearings on the front side in the axis P direction and the rear side in the axis P direction of the rotating body 11, the radial bearings support both ends of the rotating body 11. Therefore, the radial load of the rotating body 11 can be held in a more stable manner.

Industrial Applicability

As described above, the blood pump and the pump unit according to the present invention are configured to rotatably support an impeller in a casing in the radial direction in a noncontact manner and to support axial thrust load at low manufacturing cost, thereby suitable for enabling rotation also in the axial direction in a noncontact manner.

The invention claimed is:

1. A blood pump comprising:
   a rotating body rotatably placed inside a casing
   a magnetic coupling functioning as an axial bearing including a driven magnet that is a permanent magnet provided to the rotating body and a drive magnet that is a permanent magnet placed face to face with the driven magnet in a radial direction of the rotating body outside the casing to be magnetically coupled with the driven magnet;
   a drive that rotatably drives the drive magnet about an axis of the rotating body;
   a radial bearing that is a dynamic bearing having annular bearing surfaces centering on the axis on an inner wall of the casing and the rotating body, each of the annular bearing surfaces being arranged with a gap between the drive magnet and the driven magnet in the radial direction of the rotating body; and
   a closed impeller including a front shroud arranged on a front side in the axis direction in the rotating body, a rear shroud arranged on a rear side in the axis direction of the front shroud, and a vane arranged between the front shroud and the rear shroud, wherein
   the driven magnet is provided to a cylindrical shaft included in the rotating body, and the drive magnet is arranged outside in a radial direction of the shaft with respect to the driven magnet.

2. The blood pump according to claim 1, wherein the radial bearing is also arranged as the dynamic bearing, besides between the rotating body and the inner wall of the casing on the rear side of the rear shroud that is between the drive magnet and the driven magnet, between the rotating body and the inner wall of the casing on the front side of the front shroud.

3. The blood pump according to claim 1, wherein the blood pump is configured to have:
   a pump unit in which the rotating body including the driven magnet is placed inside the casing, and the radial bearing is provided between the rotating body and the inner wall of the casing, and
   a driving unit that includes the drive magnet and the drive, and
   the pump unit is detachably provided to the driving unit.

4. A pump unit of a blood pump that includes a rotating body rotatably placed inside a casing and is detachably provided to a driving unit rotatably driving the rotating body, the pump unit comprising:
   a driven magnet that is a permanent magnet provided to the rotating body in a face-to-face manner in a radial direction of the rotating body with a drive magnet that is a permanent magnet of the driving unit provided outside the casing to be rotatably driven about an axis of the rotating body, the driven magnet being magnetically coupled with the drive magnet to be a magnetic coupling functioning as an axial bearing;
   a radial bearing that is a dynamic bearing having annular bearing surfaces centering on the axis on an inner wall of the casing and the rotating body, each of the annular bearing surfaces being arranged with a gap between the drive magnet and the driven magnet in the radial direction of the rotating body; and
   a closed impeller including a front shroud arranged on a front side in the axis direction in the rotating body, a rear shroud arranged on a rear side in the axis direction of the front shroud, and a vane arranged between the front shroud and the rear shroud, wherein
   the driven magnet is provided to a cylindrical shaft included in the rotating body, and the drive magnet is arranged outside in a radial direction of the shaft with respect to the driven magnet.

* * * * *